United States Patent [19]
Clay

[11] Patent Number: 5,934,296
[45] Date of Patent: Aug. 10, 1999

[54] LIQUID APPLICATOR

[76] Inventor: Julie E. Clay, 733 14th St. S.W., Massillon, Ohio 44647

[21] Appl. No.: 08/883,982

[22] Filed: Jun. 27, 1997

[51] Int. Cl.⁶ .................................................. A45D 40/76
[52] U.S. Cl. .............................. 132/320; 401/6; 401/205; 401/281; 251/205
[58] Field of Search ................................... 132/320, 317, 132/218, 74.5; 401/6, 140, 205, 199, 198, 280, 281, 207; 251/205, 297

[56] References Cited

U.S. PATENT DOCUMENTS

| | | | |
|---|---|---|---|
| 455,567 | 7/1891 | Kraft | 401/6 |
| 540,884 | 6/1895 | Stout et al. . | |
| 721,821 | 3/1903 | Myers | 251/205 |
| 1,028,011 | 5/1912 | Ferenczy | 401/280 |
| 1,134,037 | 3/1915 | Daniels . | |
| 1,206,469 | 11/1916 | Rockwell | 251/297 |
| 1,292,288 | 1/1919 | Fisher | 401/280 |
| 1,506,305 | 8/1924 | Kelly | 401/205 |
| 1,629,905 | 5/1927 | Bjorkholtz . | |
| 1,890,599 | 12/1932 | Cobello | 401/205 |
| 1,892,260 | 12/1932 | Wick | 251/205 |
| 2,306,482 | 12/1942 | Livingston . | |
| 2,496,071 | 1/1950 | Sullivan . | |
| 2,567,764 | 9/1951 | Davies | 401/207 |
| 2,742,660 | 4/1956 | Van Esley | 401/205 |
| 3,981,106 | 9/1976 | Gallo | 401/205 |
| 4,225,254 | 9/1980 | Holberg et al. | 401/6 |
| 4,229,116 | 10/1980 | Moore . | |
| 4,483,636 | 11/1984 | Meyer . | |
| 4,553,871 | 11/1985 | Niles | 401/281 |
| 4,943,176 | 7/1990 | Baker . | |
| 4,961,661 | 10/1990 | Sutton et al. | 401/6 |
| 5,087,138 | 2/1992 | Terbrusch et al. . | |
| 5,114,256 | 5/1992 | Lin . | |
| 5,199,808 | 4/1993 | Gueret . | |
| 5,299,877 | 4/1994 | Birden . | |
| 5,322,382 | 6/1994 | Hull et al. | 401/140 |
| 5,353,819 | 10/1994 | Kahn et al. . | |
| 5,388,700 | 2/1995 | Per-Lee . | |
| 5,454,659 | 10/1995 | Vosbikian et al. | 401/207 |
| 5,493,749 | 2/1996 | Zayas . | |
| 5,568,669 | 10/1996 | Godown . | |

FOREIGN PATENT DOCUMENTS 18883   9/1908   United Kingdom ................... 401/198

Primary Examiner—Todd E. Manahan
Assistant Examiner—Eduardo C. Robert
Attorney, Agent, or Firm—Sand & Sebolt

[57] ABSTRACT

A liquid applicator having a curved hollow handle and a sponge head assembly. Liquid is poured into the hollow handle or the hollow handle is threadably secured to a threaded neck of a bottle. The sponge head assembly removably mounts to a dispensing end of the hollow handle and includes a base and a sponge. A pair of aligned holes are formed in the dispensing end of the handle and the base of the sponge head assembly for allowing liquid contained within the handle to flow therethrough and be absorbed by the sponge. A valve assembly is provided to adjust the flow of the liquid from the handle to the sponge. The valve assembly may include a dial formed with a plurality of different-sized holes. The dial is rotatable between a fully open position, a closed position or several intermediate positions. Alternatively, the valve assembly may include a slide plate having a tapered opening. Different portions of the tapered opening may be aligned with the holes of the dispensing end and sponge head assembly allowing a user to adjust the flow rate of the liquid therethrough.

7 Claims, 9 Drawing Sheets

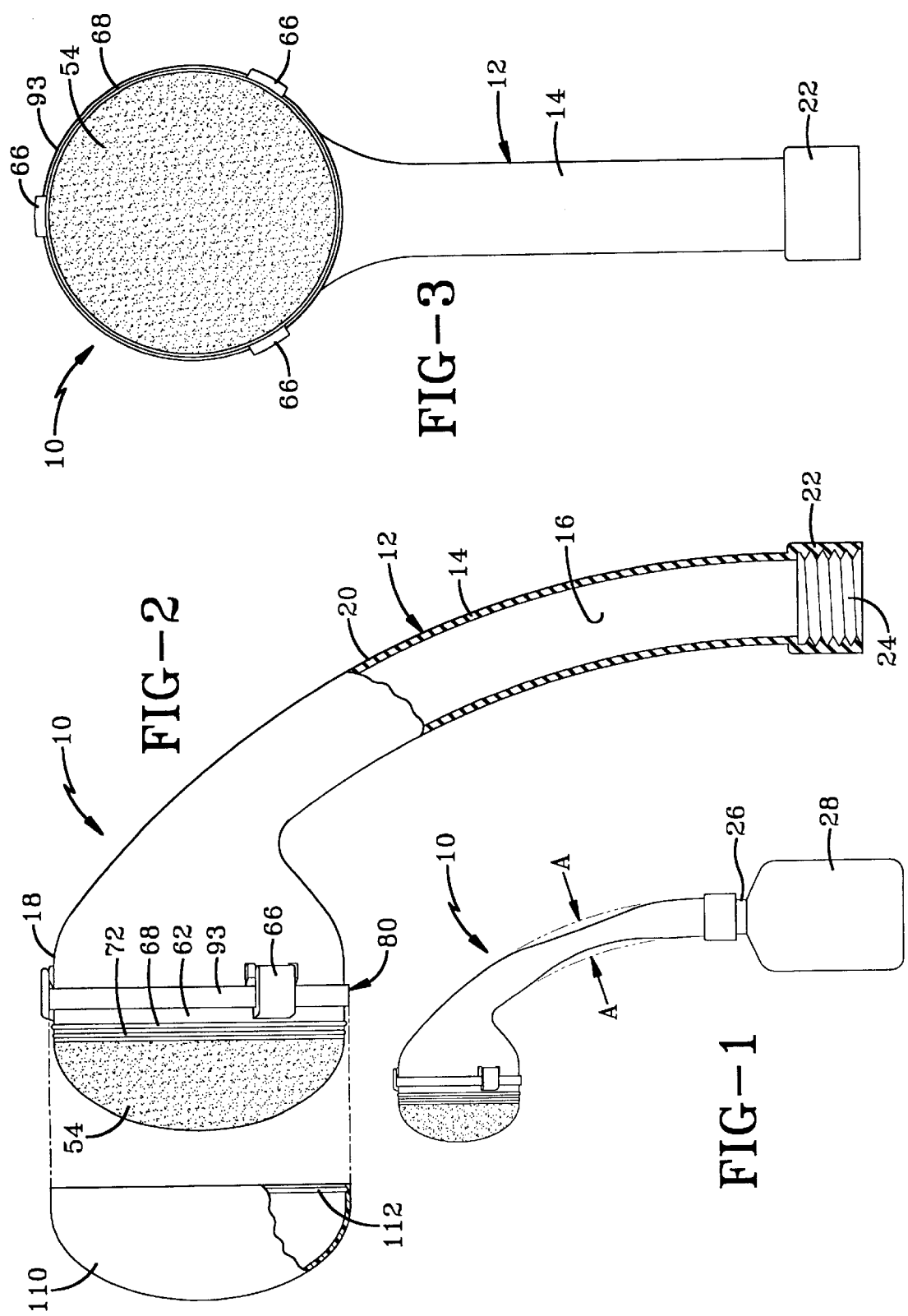

LIQUID APPLICATOR

BACKGROUND OF THE INVENTION

1. Technical Field

Generally, the invention relates to an applicator. Particularly, the invention relates to a liquid applicator for applying lotions or oils. More particularly, the invention relates to a liquid applicator having a hollow handle and a sponge head attached to an applicator end of the handle. A hole is formed in the applicator end of the handle through which the liquid contained in the handle flows to be absorbed by the sponge head.

2. Background Information

Applying suntan lotion or oil to oneself is a very messy process. Typically, a user dumps a quantity of suntan oil or lotion onto his or her hands and applies the lotion or oil to various areas of the body. Upon completion of applying the suntan lotion, the user's hands are covered with a greasy film which is difficult to remove. The user then transfers this oil from his or her hands to any item that the user may touch or pick up, possibly staining the item.

Suntan lotions and oils are often applied at a beach where the user is lying or sitting in sand. After the user has applied the lotion or oil to his or her body, the greasy or oily film attracts the granular sand and causes sand to stick to the user's hands. The user then transfers this sand to any object that he or she touches or picks up. A further problem is presented when the user is alone at the beach and wishes to apply suntan lotion or oil to his or her back. The user is able to apply the lotion or oil to the lower portion of his or her back and across his or her shoulder's, leaving an upper to upper middle portion of the user's back free of oil or lotion and exposed to the sun. Various lotion applicators have been invented which assist a user in applying lotion or oil to his or her back in a clean manner which leaves the user's hands free of a greasy or oily film.

U. S. Pat. No. 4,483,636 discloses a suntan oil applicator having an elongated hollow tubular handle with a capped end and an applicator end. The applicator end includes an enlarged ellipsoidal structure formed with orifices which allow the liquid to flow from the hollow handle to a dispensing head. The dispensing head snap fits onto the applicator end of the handle and includes a flat application surface formed with additional orifices which allow the fluid to flow through the dispensing head to a compressible porus pad. The pad absorbs and dispenses the liquid.

U. S. Pat. No. 5,087,138 discloses a suntan oil applicator having an elongated hollow handle with a capped end and an applicator end. A flat head formed with a central aperture is connected to the applicator end. A resilient absorbent pad is affixed to the bottom of the head to absorb and dispense the liquid contained in the hollow handle. A lotion release valve may be provided in the central aperture of the head whereby an upward pressure on the absorbent pad opens the valve and releases the fluid through the aperture.

U. S. Pat. No. 5,199,808 discloses a device for application of a liquid or pasty product to a surface, which includes a receptacle having an outlet opening which is sealed by a thin cover. A foam ring rests on an outer surface of the thin cover and is enclosed within the receptacle by an applicator cap. The applicator cap snap fits with the receptacle and includes a plurality of openings through which the fluid is dispensed. A round or ellipsoidal ball contained within the foam ring and applicator element, whereby a pressure is applied to the ball in the direction of the thin cover causing the ball to perforate the thin cover, opening the covered receptacle and providing access for the fluid contained within the receptacle to the openings of the applicator cap.

U. S. Pat. No, 5,299,877 discloses a liquid applicator having a liquid-holding container with an applicator secured thereto. The applicator includes a mounting block having a liquid control membrane formed with a normally closed slit. The slit opens to form a fluid outlet when the membrane is twisted and deformed by a bending force applied to the applicator. A sponge pad is attached to the top of the mounting block to absorb and dispense the fluid. In an alternative embodiment, a gate-type valve replaces the membrane to selectively control the fluid flow from the container to the applicator and thus control the dispensing of the fluid through the sponge pad.

U. S. Pat. No. 5,353,819 discloses a lotion wand having a cap sized to engage a threaded neck of a suntan lotion bottle, an applicator for dispensing the suntan lotion and a hollow tube extending between and communicating with both the cap and the applicator. The sponge is attached to the applicator and has a central aperture formed therein for allowing the lotion to be squeezed through the hollow tube and be absorbed by the sponge. A cover which snap fits with the applicator is provided to protect the applicator and sponge. A plug extends from the cover and fits within the aperture to close the aperture and prevent lotion from flowing therethrough when the lotion wand is not in use. An elongated sleeve cap extends over the applicator, tube and cap to protect the hollow tube and applicator when the lotion wand is stored.

These prior art liquid applicators are adequate for the purpose for which they are intended but these lotion applicators are not curved in a sufficient configuration which allows a person to easily apply lotion or oil to his or her back. Further, these applicators do not disclose a valve assembly which allows the person to selectively adjust the flow rate of the liquid based on the viscosity of the lotion or oil being dispensed therefrom.

Therefore, the need exists for a liquid applicator having a curved handle which allows a person to easily apply lotion or oil to his or her entire back, which include a valve assembly for controlling the flow of lotion or oil from the hollow handle of the applicator to the applicator sponge head, and in which the hollow handle is formed of a resilient material allowing the liquid to be squeezed from the handle where it is absorbed and dispensed by the sponge head.

SUMMARY OF THE INVENTION

Objectives of the invention include providing an improved liquid applicator which allows a person to apply lotion or oil to his or her entire back.

A further objective is to provide a lotion applicator in which the flow of liquid therefrom may be adjusted according to the viscosity of the liquid.

A further objective is to provide a liquid applicator which either stores the liquid within in the hollow handle thereof or which attaches directly to a threaded neck of a lotion or oil bottle allowing the lotion or oil to be dispensed directly from the bottle.

A further objective is to provide a liquid applicator in which the liquid is dispensed from the handle to the sponge head thereof by squeezing the resilient flexible handle.

Another objective is to provide a liquid applicator in which the sponge head is removable and replaceable.

A still further objective is to provide a liquid applicator in which the liquid is sealed within the hollow handle until selectively dispensed by a user.

Another objective of the invention is to provide a liquid applicator which has an outer cover to cover and protect the sponge head from dirt, debris and damage.

Another objective is to provide a liquid applicator which is of simple construction, which achieves the stated objectives in a simple, effective and inexpensive manner, which solves problems and satisfies need existing in the art.

These objectives and advantages are obtained by the improved liquid applicator of the present invention, the general of which may be stated as including a hollow tubular handle having a dispensing end and an open end, said handle being adapted to hold a liquid; an opening formed in the dispensing end of the handle; a sponge attached to the dispensing end of the handle; and a valve assembly which engages the dispensing end of the handle for controlling the flow of the liquid from the handle to the sponge.

BRIEF DESCRIPTION OF THE DRAWINGS

Preferred embodiments of the invention, illustrative of the best mode in which applicant has contemplated applying the principles, are set forth in the following description and are shown in the drawings and are particularly and distinctly pointed out and set forth in the appended claims.

FIG. 1 is a side elevational view of the liquid applicator of the present invention threadably secured to a lotion bottle and showing the resilient handle in a squeezed position for dispensing the liquid;

FIG. 2 is an exploded side elevational view of the liquid applicator of FIG. 1 with a portion in section to show the hollow handle and threads thereof and to show the snap-fit arrangement between the outer cover and the sponge head assembly;

FIG. 3 is a front elevational view of the liquid applicator;

Similar numerals refer to similar parts throughout the drawings.

DESCRIPTION OF THE PREFERRED EMBODIMENTS

Figure 4:
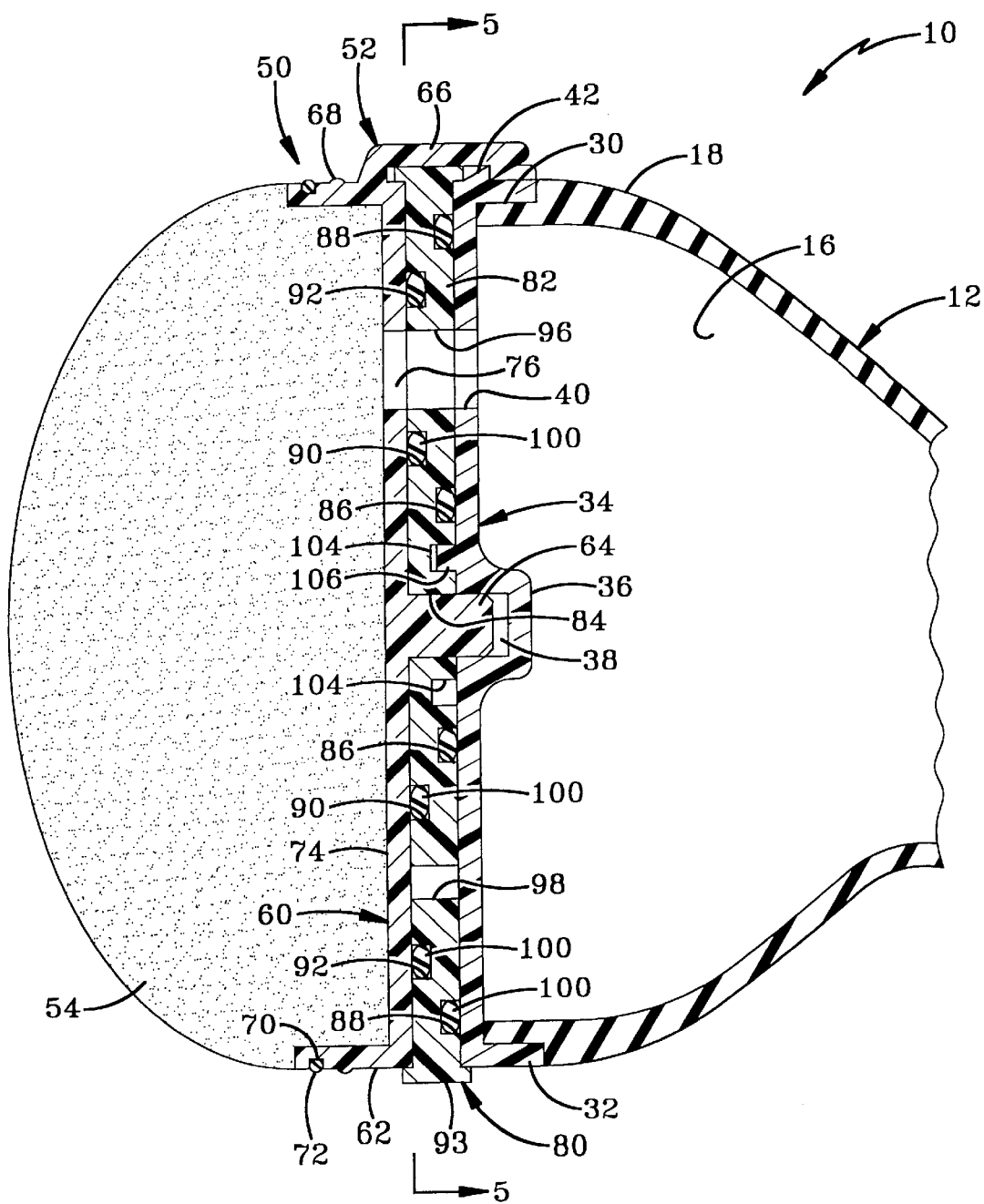
FIG. 4 is a greatly enlarged fragmentary sectional view showing the snap-fit arrangement of the sponge head and valve assembly to the dispensing end of the handle.

The liquid applicator of the present invention is shown in FIGS. 1–3 and is indicated generally at 10. Liquid applicator 10 includes a curved hollow handle 12 having a tubular wall 14 which forms an inner fluid chamber 16. Handle 12 includes an enlarged dispensing end 18, a curved elongated neck 20 and an internally threaded open end 22. Handle 12 is preferably formed of a resilient plastic material which allows neck 20 to be squeezed in the direction of arrows A (FIG. 1) to dispense the liquid contained therein through dispensing end 18, as described below. Open end 22 has an outer diameter slightly larger than that of neck 20 to allow threads 24 of open end 22 to have an inner diameter measured between the innermost point thereof, which is substantially equal to the inner diameter of neck 20. Threads 24 are formed in end 22 to engage a threaded neck 26 of a usual suntan oil or suntan lotion bottle 28. Alternatively, an externally threaded cap (not shown) could fit within end 22 to close chamber 16 thus allowing handle 12 to hold a predetermined amount of liquid.

Dispensing end 18 is formed with an outer annular cutout 30 (FIG. 4) which receives an annular flange 32 of a circular plate or front wall 34. Front wall 34 includes a central inwardly extending nub 36 formed with a circular recess 38. A circular hole 40 is formed in front wall 34 between nub 36 and the peripheral edge of front wall 34. A plurality of outwardly extending tabs 42 (FIGS. 4 and 5) are formed on the outer surface of annular flange 32 of front wall 34. Although annular flange 32 of front wall 34 could be integrally formed with dispensing end 18 of hollow handle 12, in the preferred embodiment front wall 34 is a separate member formed of a substantially more rigid material than resilient squeezable hollow handle 12 allowing dispensing end 18 to support a sponge head assembly 50, as described below.

Sponge head assembly 50 includes a sponge head support 52 which snap-fits with tabs 42 for supporting a sponge 54. Support 52 includes a generally circular-shaped base 60 having an outwardly extending annular flange 62, an inwardly extending cylindrical post 64 and a plurality of clips 66 which extend rearwardly from flange 62 and which engage tabs 42 of front wall 34. An annular rib 68 extends outwardly from the periphery of flange 62 adjacent clips 66. An annular groove 70 is formed in flange 62 adjacent rib 68 for receiving a circular seal 72. Sponge 54 is glued or otherwise attached to an outer surface 74 of base 60 within flange 62. A circular hole 76 is formed in base 60 and aligns with hole 40 of front wall 34.

Figure 5:
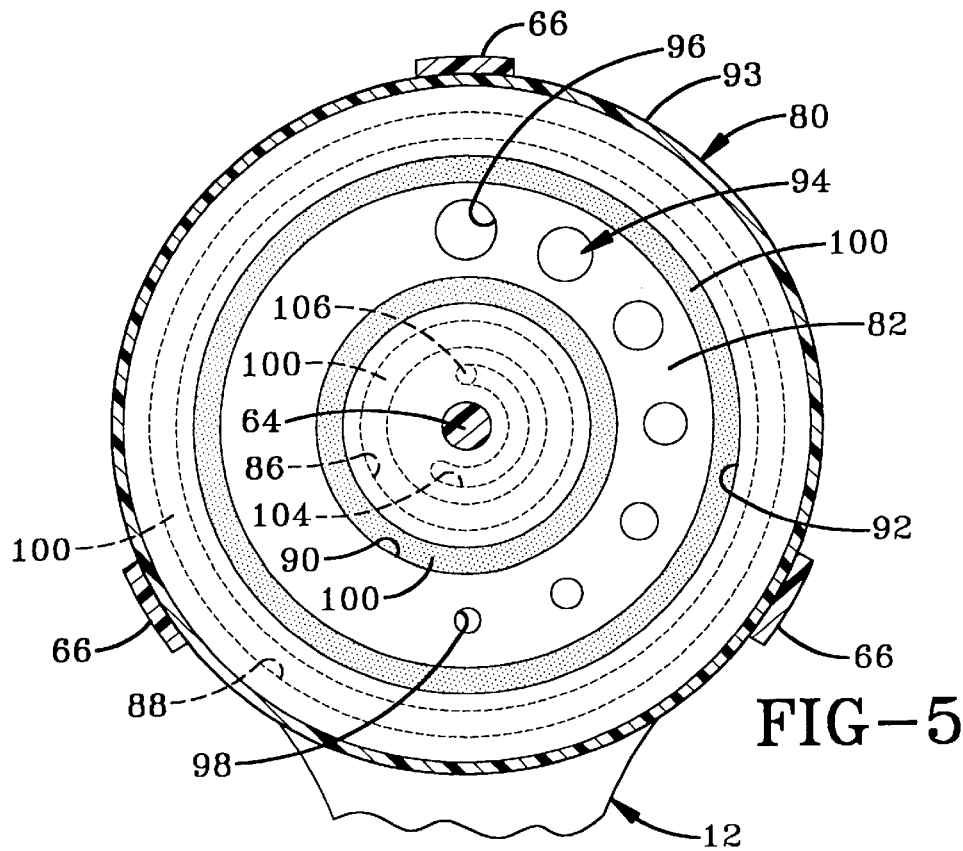
FIG. 5 is a front sectional view taken along line 5—5, FIG. 4, showing the valve assembly in an open position.

In accordance with one of the features of the invention, a valve assembly 80 is sandwiched between sponge head assembly 50 and dispensing end 18 of hollow handle 12 for controlling the flow of liquid through holes 40 and 76. Valve assembly 80 includes a generally circular plate or dial 80 formed with a central opening 84 which aligns with recess 38 for receiving post 64 of sponge head assembly 50. Dial 82 has an enlarged periphery 93 which extends outwardly over front wall 34 and base 60 and which includes a ribbed outer gripping surface to facilitate manual rotation of dial 82 as described below. A plurality of differently sized holes 94 are formed in dial 82 in a semi-circular manner to control the flow rate of the liquid through holes 40 and 76 of front wall 34 and base 60, respectively. A largest hole 96 diametrically opposes a smallest hole 98, with preferably five holes therebetween which decrease in size from largest hole 96 to smallest hole 98. Dial 82 is shown in FIGS. 4 and 5 with largest hole 96 aligned with holes 40 and 76 of front wall 34 and base 60.

Dial 82 is formed with a rear inner groove 86, a rear outer groove 88, a front inner groove 90 and a front outer groove 92. Grooves 86, 88, 90 and 92 are all circular shaped with rear grooves 86 and 88 facing front wall 34 of handle 12 and front grooves 90 and 92 facing base 60 of sponge head assembly 50. Rear outer groove 88 is formed in the rear of dial 82 adjacent the periphery thereof. Front outer groove 92 is formed opposite rear outer groove 88 between rear outer groove 88 and holes 94. Front inner groove 90 is positioned adjacent to and inside of holes 94. Rear inner groove 86 is formed opposite front inner groove 90 between front inner groove 90 and opening 84. Grooves 86, 88, 90 and 92 each receives a circular O-ring or seal 100. Seals 100 are preferably formed of a rubber material for sealing valve assembly 80 in its sandwiched relationship between front wall 34 and base 60 and prevent the liquid being dispensed by liquid applicator 10 from leaking from the sides of sponge head assembly 50. Seals 100 have a diameter slightly larger than the depth of their respective grooves, allowing seals 100 to be sandwiched between dial 82 and the respective front wall 34 and base 60 causing seals 100 to deform into the oval shape shown in FIG. 4.

A curved stop groove 104 is formed in the rear surface of dial 82 between rear inner groove 86 and opening 84. Stop groove 104 extends in a partial circle (FIG. 5) for limiting the rotational movement of dial 82. A stop tab 106 extends outwardly from front wall 34 and is received by groove 104. Stop tab 106 abuts and contacts the ends of groove 104 to limit the rotational movement of dial 82 between a fully open position and a closed position, as described below.

An outer cover or cap 110 (FIG. 2) is complementary shaped to sponge head assembly 50 and snap-fits therewith to cover and protect sponge 54 from dirt, debris and damage. Cap 110 is formed with an annular groove 112 extending around an inner surface thereof which snaps over and receives rib 68 of sponge head assembly 50 to retain cap 110 in an engaged closed position on sponge head assembly 50. Seal 72 abuts the inner surface of cap 110 to prevent liquid contained within sponge 54 from leaking from liquid applicator 10 when applicator 10 is not in use.

In use, cap 110 is removed from sponge head assembly 50 and open end 22 of curved hollow handle 12 threadably engages neck 26 of bottle 28. Bottle 28 is squeezed or tipped to displace the oil or lotion into chamber 16 of handle 12. Dial 82 is rotated to an open position wherein one of holes 94 aligns with holes 40 and 76 of front wall 34 and base 60, respectively. Dial 82 is shown in FIG. 5 with the largest hole 96 aligned with holes 40 and 76, but any of holes 94 may be aligned with holes 40 and 76 depending on the viscosity of the fluid being dispensed by liquid applicator 10 and depending upon the amount of fluid the user desires to be absorbed by sponge 54. As the fluid is squeezed from bottle 28, the fluid flows into chamber 16 of hollow handle 12 and through holes 40, 96 and 76 where it contacts and is absorbed by sponge 54. As the fluid flows into and is absorbed by sponge 54, the fluid will fill sponge 54. The user then grasps hollow handle 12 and rubs the outer surface of sponge 54 on his or her body allowing the fluid to be dispensed from sponge 54 onto the user.

Figure 6:
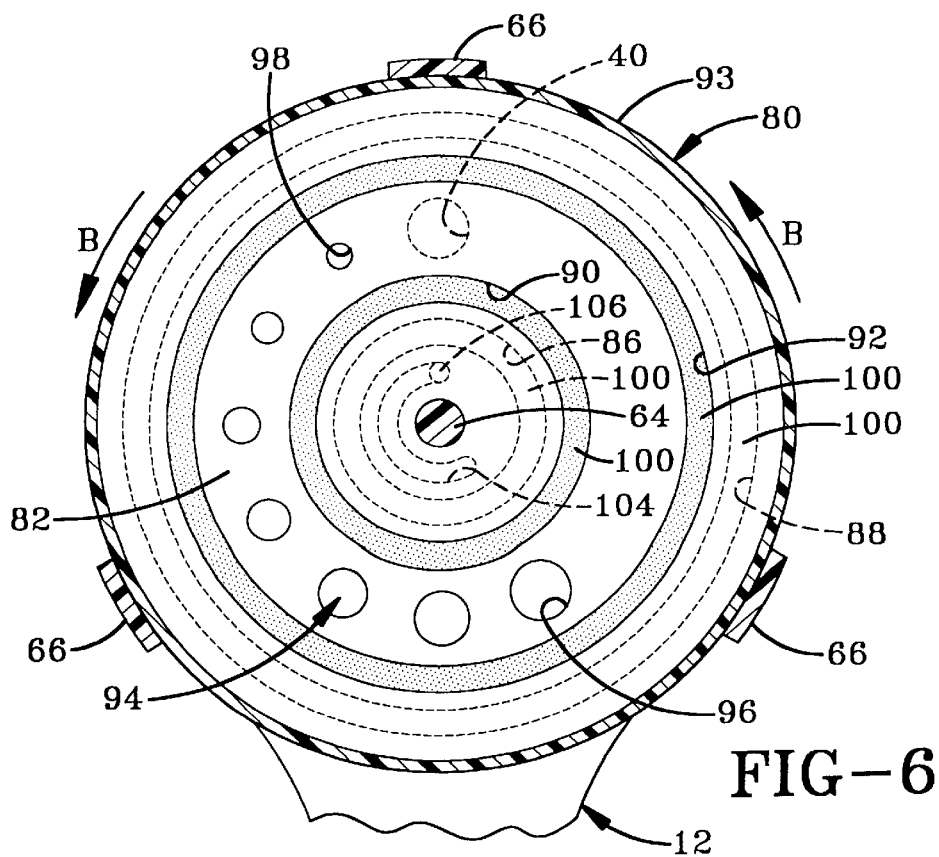
FIG. 6 is a front sectional view similar to FIG. 5 showing the valve assembly rotated to a closed position.

After use, dial 82 is rotated in the direction of arrow B (FIG. 6) whereby the flat portion of dial 82 free of holes 94 aligns with holes 40 and 76 to close liquid applicator 10 and prevent the liquid from flowing into sponge 54. Seals 100 prevent the liquid from leaking out the sides of rotatable dial 82. Cap 110 is snap-fitted back on valve assembly 80 to protect sponge 54. Hollow handle 12 may be left in its engagement with bottle 28, or the liquid contained within chamber 16 may be drained back into bottle 28 and liquid applicator 10 may be removed from its engagement with bottle 28.

Alternatively, the liquid contained within bottle 28 may be poured into chamber 16 of hollow handle 12 and a screw cap may threadably engage threads 24 of open end 22 sealing chamber 16 and retaining the liquid therein. Hollow handle 12 may be squeezed in the direction of arrows A forcing the liquid through holes 40, 96 and 76 and into sponge 54.

Sponge head assembly 50 may be removed from its engagement with dispensing end 18 of hollow handle 12 allowing a new clean sponge 54 to be attached to liquid applicator 10. Clips 66 are pried from their engagement with tabs 42 allowing sponge head assembly 50 to be removed from dispensing end 18. A new sponge head assembly 50 is positioned with base 60 thereof extending within enlarged edge 93 of dial 82. Post 64 of the new sponge head assembly 50 is inserted through opening 84 of dial 82 and into recess 38 of front wall 34. Clips 66 snap-fit with tabs 42 to retain a sponge head assembly 50 to dispensing end 18 of hollow handle 12.

Figure 7:
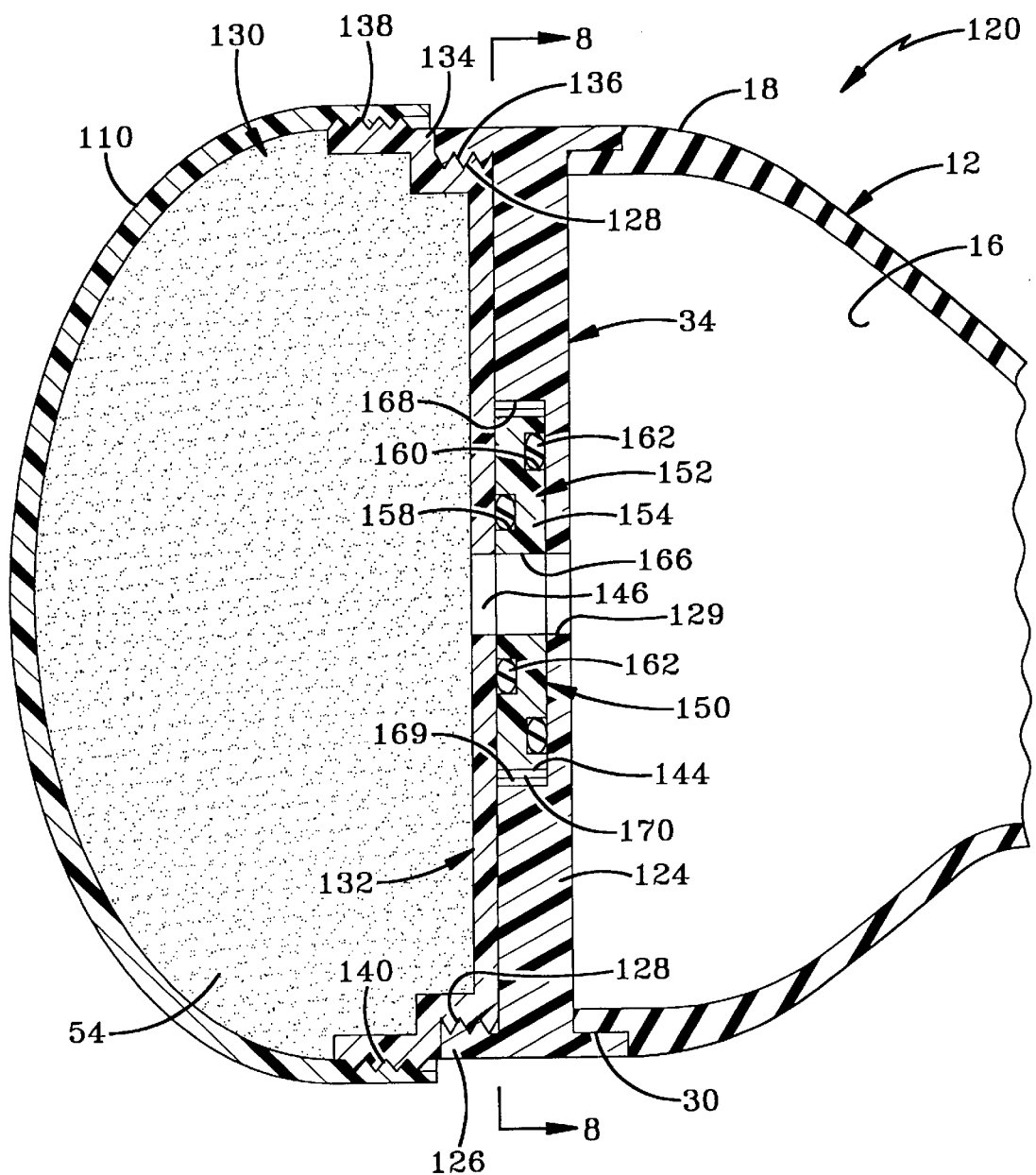
FIG. 7 is a greatly enlarged fragmentary sectional view similar to FIG. 4 showing a second embodiment of the sponge head and valve assembly attached to the dispensing end of the handle.
Figure 8:
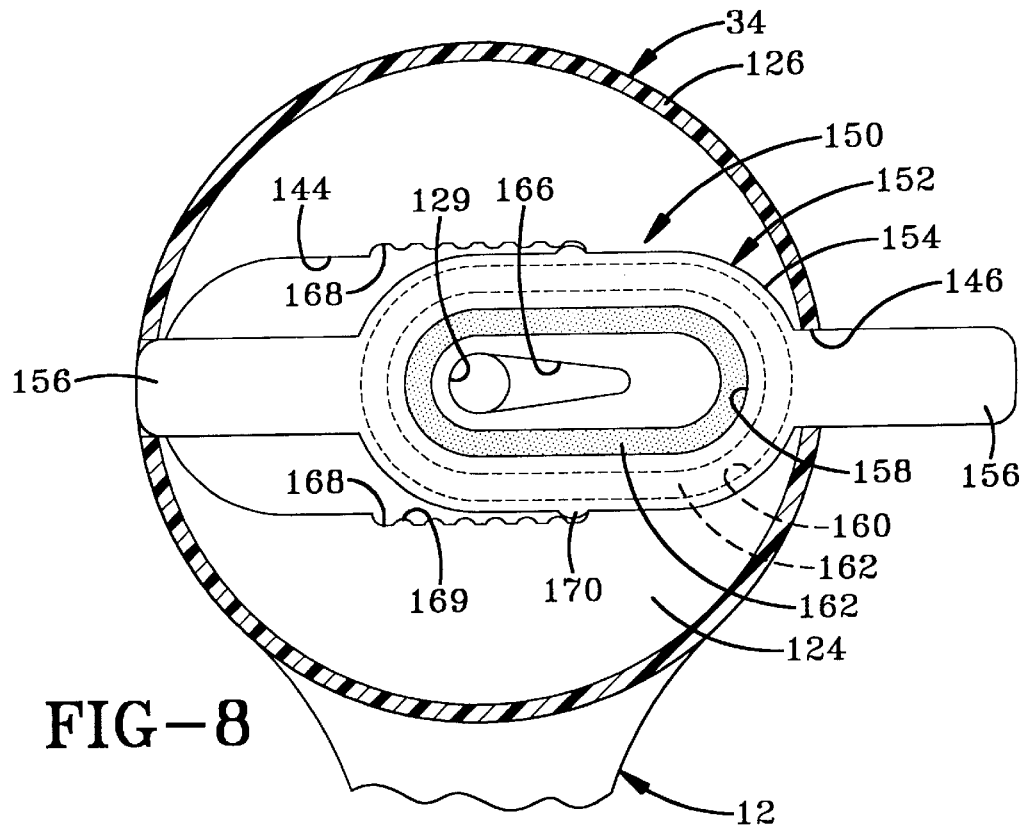
FIG. 8 is a front sectional view taken along line 8—8, FIG. 7, showing the valve assembly in an open position.
Figure 9:
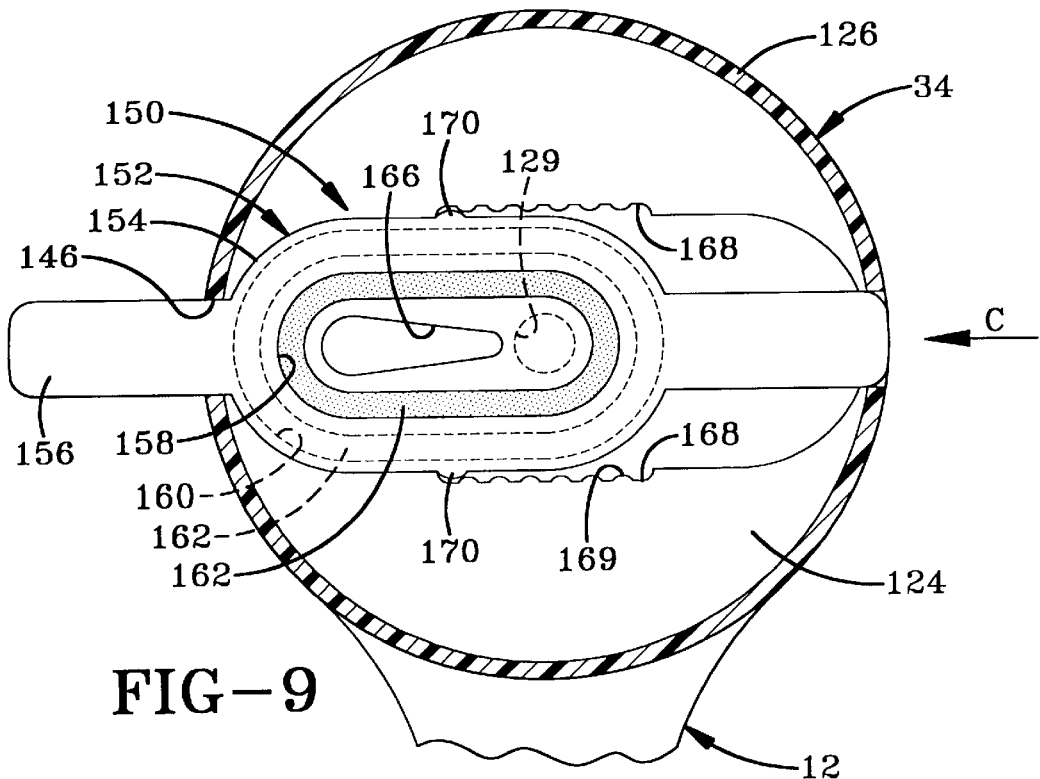
FIG. 9 is a front sectional view similar to FIG. 8 showing the second embodiment of the valve assembly in a closed position.

A second embodiment of the liquid applicator of the present invention is shown in FIGS. 7–9 and is indicated generally at 120. Dispensing end 18 of liquid applicator 120 includes a front wall 124 similar to front wall 34 of liquid applicator 10 but which includes an outwardly extending annular flange 126 having an internally threaded surface 128. Liquid applicator 120 includes a sponge head assembly 130 which is similar to sponge head assembly 50 of liquid applicator 10 but which includes a base 132 having an outwardly stepped annular flange 134. Stepped flange 134 has a threaded inner section 136 and a threaded outer section 138. Threaded inner section 136 engages inner threaded surface 128 of annular flange 126 to threadably secure sponge head assembly 130 to dispensing end 18 of liquid applicator 120. Cap 110 of liquid applicator 120 is formed with inner threads 140 adjacent the open end thereof. Threads 140 engage threaded outer section 138 of stepped flange 134 allowing cap 110 to be threadably secured to sponge head assembly 130 to protect sponge 54 from dirt, debris or damage.

Front wall 124 is formed with an enlarged recessed area 144 having a pair of opposed side slots 146 (FIGS. 8 and 9) which extend through annular flange 126. A valve assembly 150 is positioned within recessed area 144 and includes a slide plate 152 having an enlarged middle section 154 and two opposed narrower end sections 156. Middle section 154 is generally oval shaped and is formed with an oval-shaped front groove 158 (FIG. 7) and an oval-shaped rear groove 160. Grooves 158 and 160 each receives a ring-shaped seal 162 which seals valve assembly 150 and prevents liquid from leaking out the sides of liquid applicator 120. A hole 129 is formed centrally in front wall 124 for allowing liquid to flow therethrough as described below. A hole 146 is formed centrally in base 132 and is aligned with hole 129 of front wall 124. A tapered opening 166 is formed in slide plate 152 intermediate the top and bottom thereof for adjusting the flow rate of the liquid from hollow handle 12 through hole 129 and 146 and into sponge 54. Tapered opening 166 aligns with holes 129 and 146 and has a size at a widest end thereof substantially equal to the size of holes 129 and 146, and gradually tapers to a size substantially smaller than holes 129 and 146. Recess 144 is formed with top and bottom adjustment slots 168, each of which includes a plurality of spaced nubs 169. A tab 170 is formed on the top and bottom of middle section 154 of slide plate 152 and extends within slots 168. Tabs 170 cam along nubs 169 and rest in the spaces between nubs 169 for retaining slide plate 152 in an adjusted position as described below.

In use, cap 110 is unscrewed from base 132 and slide plate 152 is moved to the position of FIG. 8. The widest part of opening 166 of middle section 154 is positioned to align with holes 129 and 146 allowing fluid contained within hollow handle 12 to flow into sponge 54. The liquid within sponge 54 is dispensed in a manner similar to liquid applicator 1. After use, slide plate 152 is slid in the direction of arrow C (FIG. 9) aligning a flat solid portion of slide plate 152 with holes 129 and 146 placing liquid applicator 120 in the closed position. Tab 170 cams along nubs 169 which retain slide plate 152 in position. Nubs 169 are spaced along slots 168 whereby slide plate 152 may be retained in several adjusted positions whereby varying portions of opening 166 of slide plate 162 align with holes 129 and 146 thus controlling the amount of liquid which flows into sponge 54.

Figure 10:
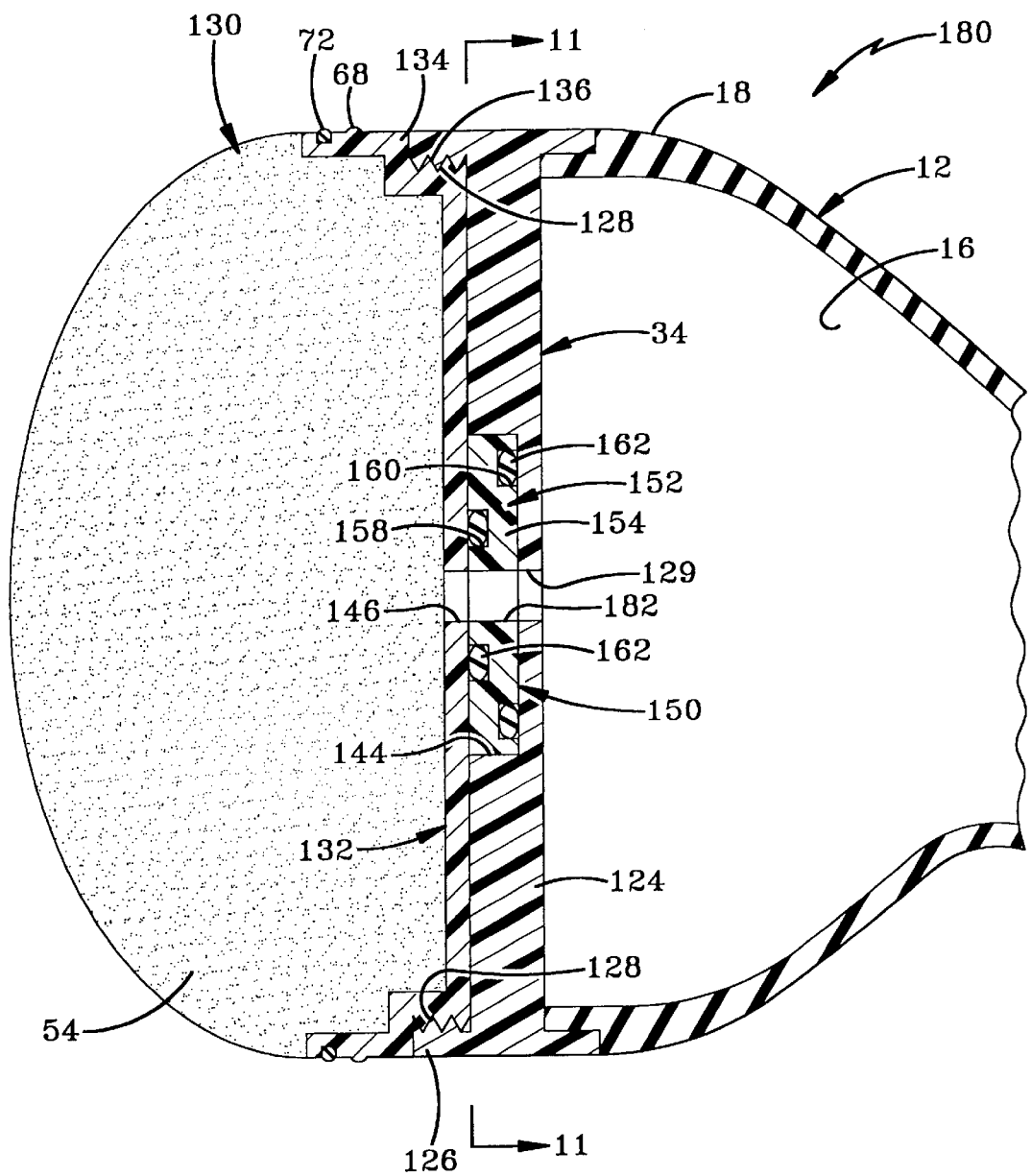
FIG. 10 is a greatly enlarged fragmentary sectional view similar to FIG. 7 showing a third embodiment of the sponge head and valve assembly attached to the dispensing end of the handle.
Figure 11:
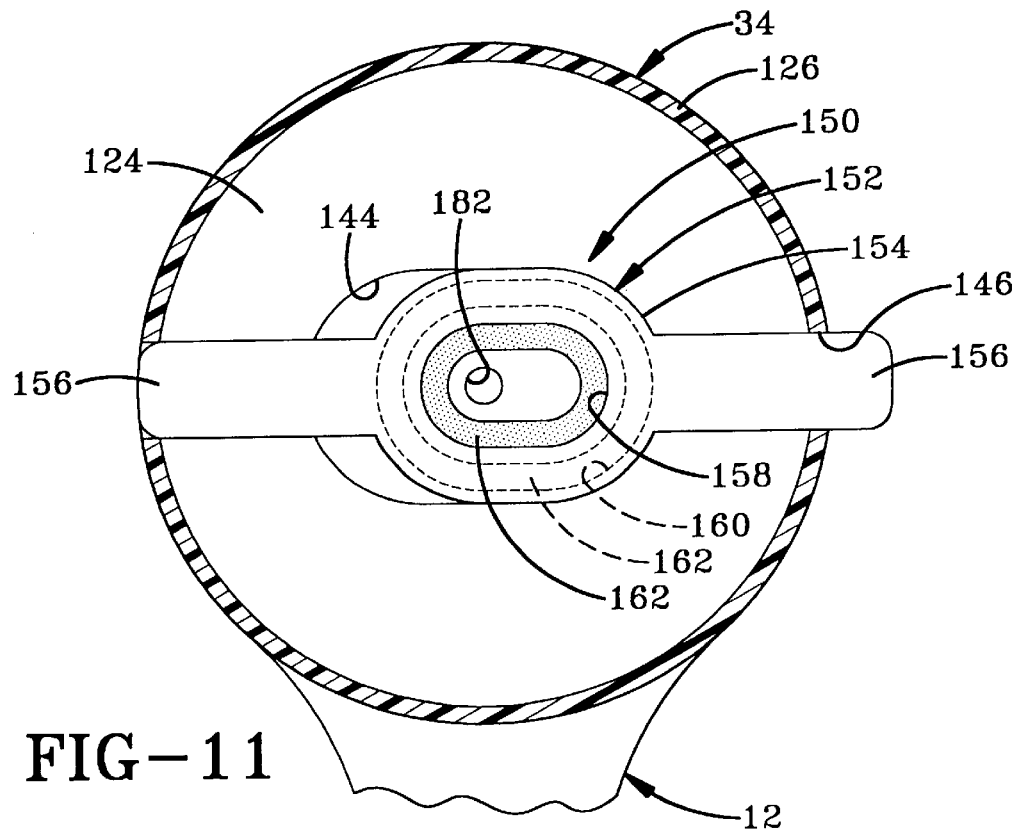
FIG. 11 is a front sectional view taken along line 11—11, FIG. 10, showing the valve assembly in an open position.
Figure 12:
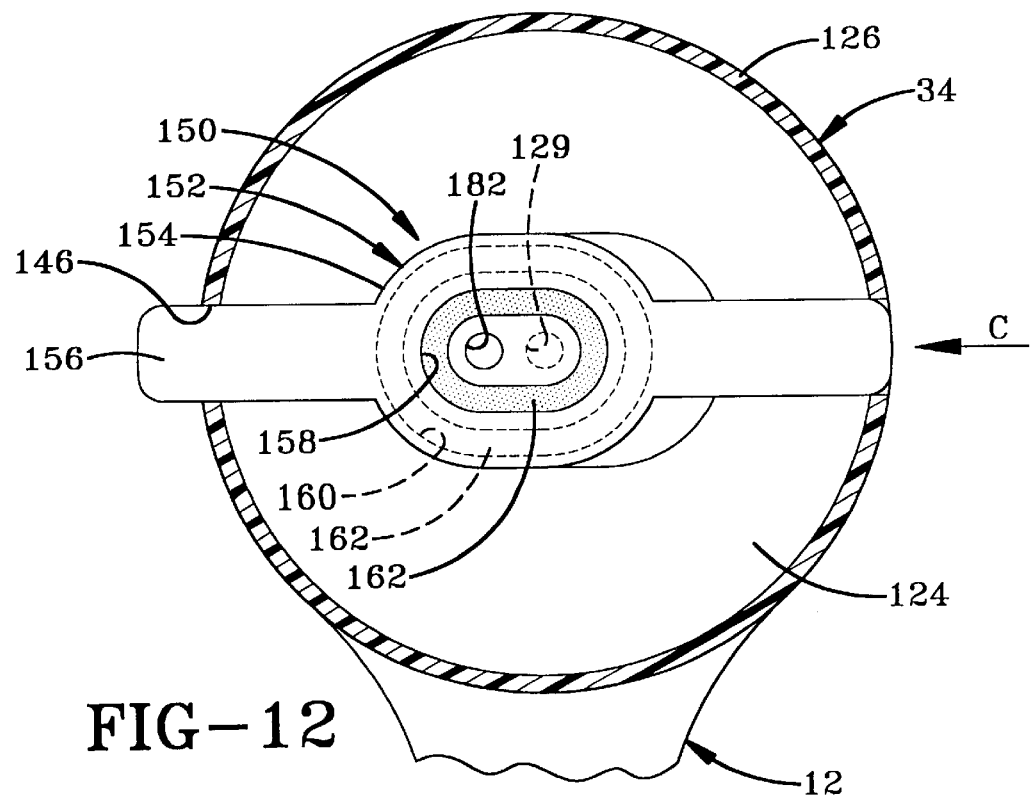
FIG. 12 is a front sectional view similar to FIG. 11 showing the third embodiment of the valve assembly in a closed position.

A third embodiment of the liquid applicator of the present invention is shown in FIGS. 10–12 and is indicated generally at 180. Liquid applicator 180 is generally similar to liquid applicator 120 and includes slide plate 152 having a single circular opening 182. Slide plate 152 slides between an open position which aligns hole 182 with holes 129 and 146 of front wall 124 and base 132, respectively, and a closed position which aligns a solid flat portion of slide plate 152 with holes 129 and 146.

Figure 13:
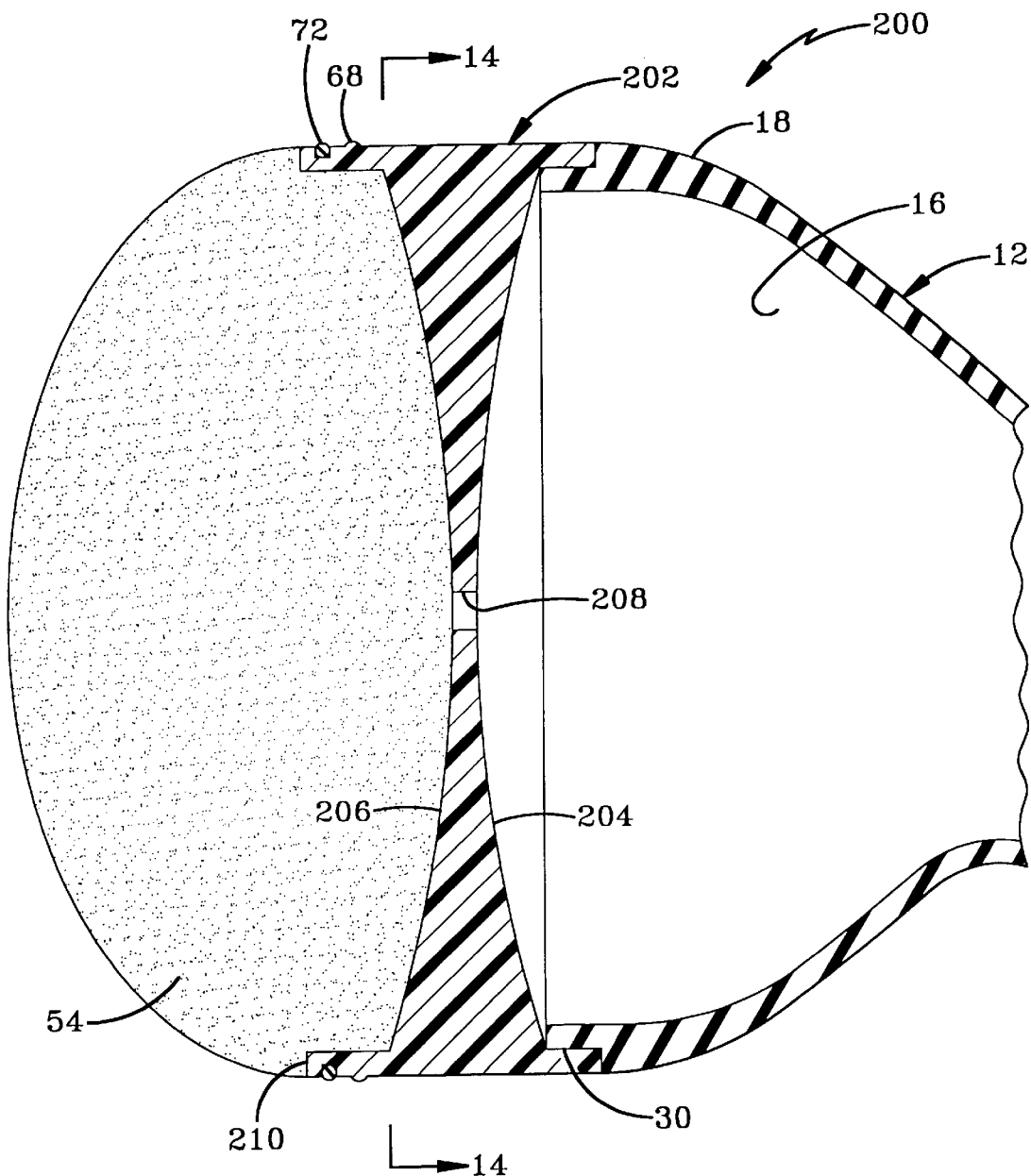
FIG. 13 is a greatly enlarged fragmentary sectional view showing a fourth embodiment of the sponge head and valve assembly attached to the dispensing end of the handle.
Figure 14:
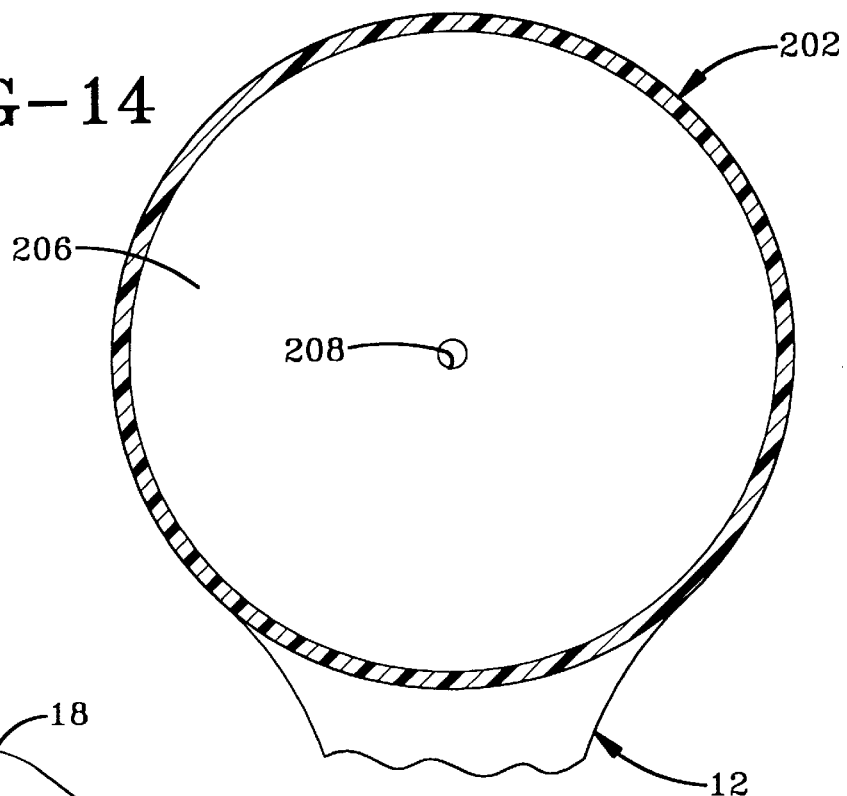
FIG. 14 is a front sectional view taken along line 14—14, FIG. 13.

A fourth embodiment of the liquid applicator is shown in FIGS. 13 and 14 and is indicated generally at 200. Liquid applicator 200 includes a front wall 202 attached to dispensing end 18 of handle 12 which has an inner concave surface 204 and an outer concave surface 206. A circular hole 208 is formed centrally in front wall 202 to allow the liquid to flow from dispensing end 18 of hollow handle 12 to sponge 54. An annular flange 210 extends outwardly from the periphery of outer surface 206 of front wall 202 for retaining sponge 54 directly to outer concave surface 206 of front wall 202. Hollow handle 12 of liquid applicator 200 is formed of a resilient material which allows handle 12 to be squeezed inwardly in a manner similar to that of liquid applicator 10 and as shown by arrows A in FIG. 1. Hollow handle 12 is filled with the liquid and a screw cap is inserted within open end 22. Handle 12 is squeezed, forcing the liquid through hole 208 and into sponge 54. When the pressure is released from handle 12, the small hole 208 and the concave surface 204 of front wall 202 will create a vacuum to retain the liquid within handle 12 and prevent further liquid from flowing through hole 208.

Figure 15:
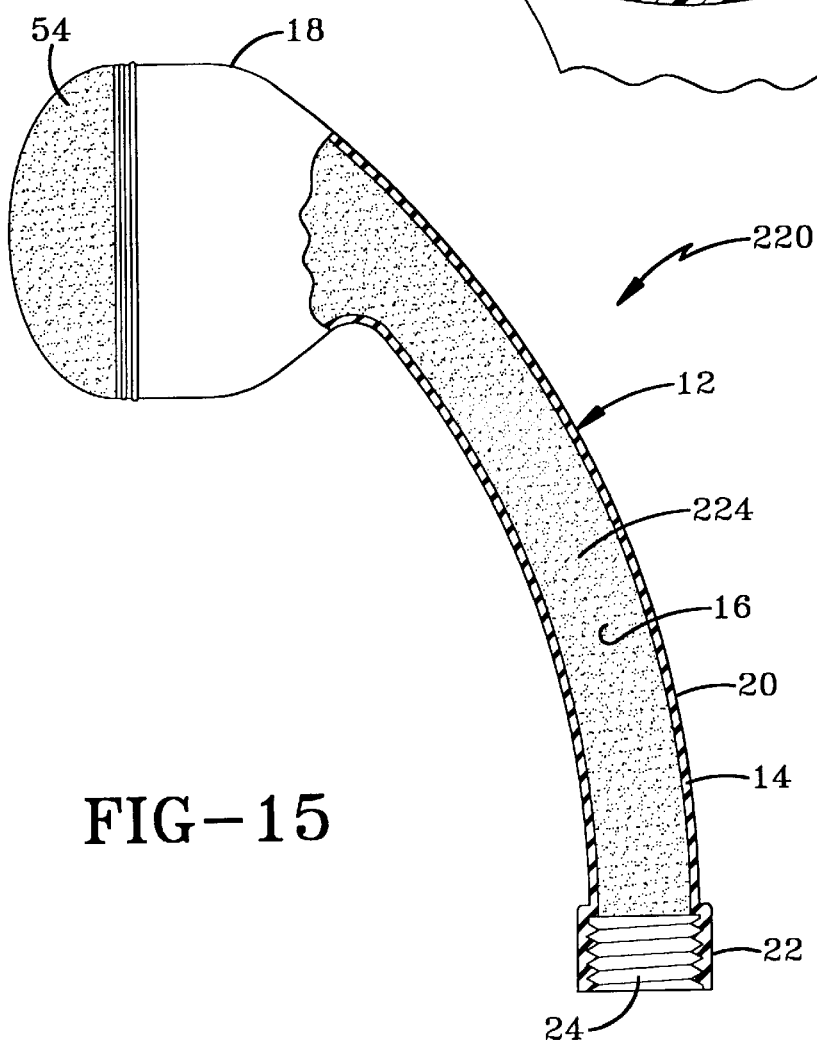
FIG. 15 is a side elevational view with a portion in section to show the hollow handle filled with a sponge material.

A fifth embodiment of the liquid applicator of the present invention is shown in FIG. 15 and is indicated generally at 220. Liquid applicator 220 is similar to liquid applicator 200 and includes handle 12 filled with a sponge material which absorbs the liquid poured within chamber 16. When handle 12 is squeezed in a manner similar to that shown by arrows A of FIG. 1, the liquid contained within sponge 224 will be squeezed out of the sponge of chamber 16 through hole 208 and into sponge 54. Sponge 224 of handle 12 absorbs the liquid contained within chamber 16 and prevents the liquid from flowing out hole 208 when liquid applicator 220 is not in use.

Accordingly, liquid applicators 10 and 120 provide a valve assembly which allows the flow of the liquid from handle 12 to sponge 54 to be incrementally changed depending on the viscosity of the liquid and the desired amount of liquid to be dispensed. Liquid applicator 180 provides a slide plate 152 slidable between an open and closed position. Liquid applicators 200 and 220 have a single hole through which the liquid is dispensed to sponge 54 when handle 12 is squeezed inwardly by a user. Screw cap 110 may include groove 112 allowing screw cap 110 to snap-fit with the sponge head assembly or screw cap 110 may be threaded to engage external threads 138 of the sponge head assemblies. Sponge head assemblies 50 and 130 are removable from dispensing end 18 of the liquid applicators allowing sponge 54 to be replaced when sponge 54 has accumulated dirt or debris or has been damaged.

Accordingly, the improved liquid applicator is simplified, provides an effective, safe, inexpensive, and efficient device which achieves all the enumerated objectives, provides for eliminating difficulties encountered with prior devices, and solves problems and obtains new results in the art.

In the foregoing description, certain terms have been used for brevity, clearness and understanding; but no unnecessary limitations are to be implied therefrom beyond the requirement of the prior art, because such terms are used for descriptive purpose and are intended to be broadly construed.

Moreover, the description and illustration of the invention is by way of example, and the scope of the invention is not limited to the exact details shown or described.

Having now described the features, discoveries and principles of the invention, the manner in which the improved liquid applicator is constructed and used, the characteristics of the construction, and the advantageous, new and useful results obtained, the new and useful structures, devices, elements, arrangements, parts and combinations, are set forth in the appended claims.

I claim:

1. A liquid applicator including:
    a hollow tubular handle having a dispensing end and an open end, said handle being adapted to hold a liquid and being formed from a resilient squeezable material so that the handle is adapted to be squeezable to cause the liquid in the handle to exit the handle through the dispensing end;
    an opening formed in the dispensing end of the handle;
    a front wall covering said opening, said front wall having an inner surface and an outer surface with both the inner and outer surfaces being concave such that the front wall has a thin area, said front wall further including a hole formed in the front wall in the thin area;
    a sponge attached to the front wall;
        whereby said front wall acts as a valve assembly for controlling the flow of the liquid from the handle to the sponge.

2. A liquid applicator including:
    a hollow tubular handle having a dispensing end and an open end, the handle being adapted to hold a liquid, the handle being fabricated from a resilient, squeezable material so that the handle may be compressed;
    an opening formed in the dispensing end of the handle;
    a base having an opening that is generally aligned with the opening in the dispensing end of the handle so that liquid may flow from the handle through the dispensing end of the handle and through the base;
    a sponge carried by the base;
    in which the handle includes a front wall at the dispensing end thereof and in which the opening is formed in the front wall;
    a valve assembly disposed between the front wall of the handle and the base that controls the flow of liquid from the handle to the sponge;

in which the valve assembly includes a slide plate slidable between open and closed positions;

in which the slide plate is formed with a hole, said hole being aligned with the opening of the dispensing end of the handle when the slide plate is in the open position;

in which the hole of the slide plate is tapered from a largest end which is substantially equal to the size of the opening of the dispensing end to a smaller end which is substantially smaller in size than the opening of the dispensing end, said slide plate being slidable to align varying portions of the tapered hole with the opening to selectively control the flow of the liquid from the handle; and in which the front wall of the dispensing end is formed with a recessed area having a length larger than the length of the slide plate, the slide plate being slidable within said recessed area.

3. The liquid applicator defined in claim 2 in which the base includes a plurality of clips; in which the dispensing end includes a plurality of tabs; and in which the clips engage the tabs to attach the base to the dispensing end.

4. The liquid applicator defined in claim 2 in which the base threadably engages the dispensing end of the handle.

5. The liquid applicator defined in claim 2 in which the handle is generally curved.

6. A liquid applicator including:

a hollow tubular handle having a dispensing end and an open end, the handle being adapted to hold a liquid, the handle being fabricated from a resilient, squeezable material so that the handle may be compressed;

an opening formed in the dispensing end of the handle; a base having an opening that is generally aligned with the opening in the dispensing end of the handle so that liquid may flow from the handle through the dispensing end of the handle and through the base;

a sponge carried by the base;

the handle including a front wall at the dispensing end thereof and in which the opening is formed in the front wall;

a valve assembly disposed between the front wall of the handle and the base that controls the flow of liquid from the handle to the sponge;

the valve assembly including a slide plate slidable between opened and closed positions;

the slide plate being formed with a hole, said hole aligning with the opening of the dispensing end of the handle when the slide plate is in the open position;

the hole of the slide plate being tapered from a largest end which is substantially equal in size to the opening of the dispensing end to a smaller end which is substantially smaller in size than the opening of the dispensing end, the slide plate being slidable to align varying portions of the tapered hole with the opening to selectively control the flow of liquid from the handle; and an outer edge of the slide plate being formed with a tab; in which an inner edge of the recessed area is formed with a plurality of spaced nubs; and in which the tab is positioned between a pair of the nubs to hold the slide plate in an adjusted position.

7. A liquid applicator in combination with a bottle of suntan lotion, the combination comprising:

a bottle of suntan lotion having a threaded neck, the threaded neck having at least one thread that projects outwardly from the threaded neck;

the liquid applicator having a hollow tubular handle having a dispensing end and an open end, the handle being adapted to hold a fluid and being fabricated from a resilient, squeezable material;

an opening formed in the dispensing end of the handle;

a sponge attached to the dispensing end of the handle;

a valve assembly that engages the dispensing end of the handle for controlling the flow of liquid from the handle to the sponge; and the open end of the handle having at least one inwardly directed thread that is configured to cooperate with the outwardly directed thread of the threaded neck so that the liquid applicator may be screwed onto the bottle of suntan lotion.

* * * * *